United States Patent
Parthasaradhi Reddy et al.

(10) Patent No.: US 8,383,811 B2
(45) Date of Patent: *Feb. 26, 2013

(54) PROCESS FOR PREPARING EFAVIRENZ POLYMORPH

(75) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Kesireddy Subash Chander Reddy, Hyderabad (IN)

(73) Assignee: Hetero Research Foundation (IN)

( * ) Notice: Subject to any disclaimer, the term of this patent is extended or adjusted under 35 U.S.C. 154(b) by 19 days.

This patent is subject to a terminal disclaimer.

(21) Appl. No.: 12/863,808

(22) PCT Filed: Dec. 22, 2008

(86) PCT No.: PCT/IN2008/000855
§ 371 (c)(1),
(2), (4) Date: Jul. 21, 2010

(87) PCT Pub. No.: WO2010/073254
PCT Pub. Date: Jul. 1, 2010

(65) Prior Publication Data
US 2012/0232069 A1   Sep. 13, 2012

(51) Int. Cl.
*C07D 265/18* (2006.01)
*A61K 31/535* (2006.01)

(52) U.S. Cl. ...................................... 544/92; 514/230.5
(58) Field of Classification Search .................... 544/92; 514/230.5
See application file for complete search history.

(56) References Cited

U.S. PATENT DOCUMENTS

| | | | |
|---|---|---|---|
| 5,519,021 A | 5/1996 | Young et al. | |
| 5,665,720 A * | 9/1997 | Young et al. | 514/230.5 |
| 8,242,267 B2 * | 8/2012 | Parthasaradhi Reddy et al. | 544/92 |

FOREIGN PATENT DOCUMENTS

| | | |
|---|---|---|
| WO | 9833782 A1 | 8/1998 |
| WO | 9964405 A1 | 12/1999 |
| WO | 2006018853 A2 | 2/2006 |
| WO | 2006040643 A2 | 4/2006 |
| WO | 2008108630 A1 | 9/2008 |

OTHER PUBLICATIONS

PCT Written Opinion of the International Searching Authority and International Preliminary Report of Patentability of International application No. PCT/IN2008/000855 dated Oct. 20, 2011.
International Preliminary Report on Patentability and Written Opinion; International Application No. PCT/IN2008/000855; International Filing Date Dec. 22, 2008; Date of Mailing Oct. 20, 2011; 5 pages.
International Search Report; International Application No. PCT/IN2008/000855; International Filing Date Dec. 22, 2008; Published Dec. 8, 2011; 3 pages.

* cited by examiner

*Primary Examiner* — Kahsay T Habte
(74) *Attorney, Agent, or Firm* — Cantor Colburn LLP

(57) ABSTRACT

The present invention relates to a process for the preparation of crystalline non-hygroscopic form H1 of efavirenz, and pharmaceutical compositions containing it. In accordance with the present invention efavirenz was dissolved in acetone at 25° C.-30° C., the solution was slowly added to water at 0° C.-5° C., the separated solid was filtered, washed with mixture of acetone and water and dried at 25° C.-35° C. under below 65% relative humidity for 18 hours to give crystalline non-hygroscopic efavirenz form H1.

7 Claims, 1 Drawing Sheet

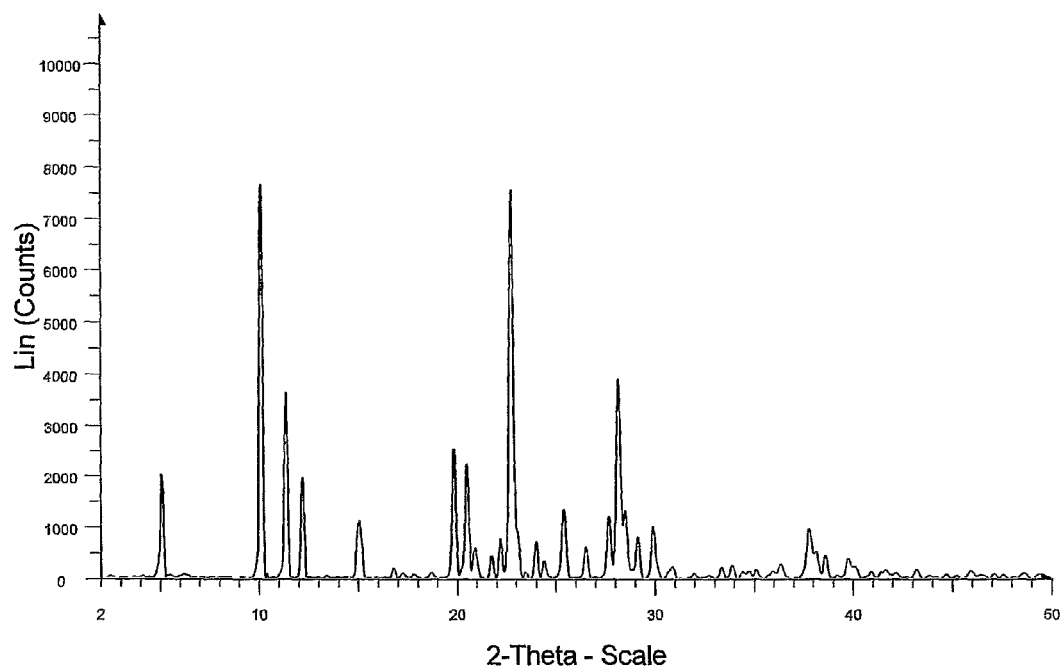

PROCESS FOR PREPARING EFAVIRENZ POLYMORPH

FIELD OF THE INVENTION

The present invention relates to a process for preparation of crystalline non-hygroscopic efavirenz form H1, and pharmaceutical compositions containing it.

BACKGROUND OF THE INVENTION

Pharmaceutical products with HIV reverse transcriptase (including its resistant varieties) inhibitors are described in U.S. Pat. No. 5,519,021. An especially important compound among those disclosed is efavirenz, (4S)-6-chloro-4-(cyclopropylethynyl)-1,4-dihydro-4-(trifluoromethyl)-2H-3,1-benzoxazin-2-one. Efavirenz has the following structural formula:

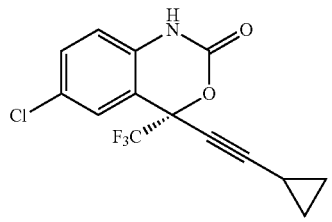 [SMILES: O=C1Nc2ccc(Cl)cc2[C@@](C#CC2CC2)(C(F)(F)F)O1]

This compound is used for the preparation of a medicament having nonnucleoside HIV-1 reverse transcriptase inhibiting activity that is useful in the prevention or treatment of infection by HIV and the treatment of AIDS. Efavirenz is sold commercially as SUSTIVA® by Bristol Myers Squibb.

WO patent application publication No. 98/33782 disclosed three crystalline forms, Form I (characterized by an x-ray powder diffraction patterns having peaks expressed as 2θ at 6.1, 6.4, 10.4, 10.9, 12.3, 13.2, 14.2, 15.2, 16.9, 18.4, 19.2, 20.1, 21.2, 22.3, 23.0, 24.9, 25.9, 26.3, 27.2, 28.1, 28.6, 29.1, 29.5, 30.7, 32.4 and 38.3 degrees), Form II (characterized by an x-ray powder diffraction patterns having peaks expressed as 2θ at 3.6, 6.3, 11.1, 12.8, 13.3, 14.3, 16.1, 16.9, 18.5, 19.2, 19.6, 20.6, 21.3, 22.6, 23.2, 24.4, 24.9, 26.0, 26.8, 27.6, 28.4, 29.2, 29.6, 30.6, 31.9 and 33.8 degrees) and Form III (characterized by an x-ray powder diffraction patterns having peaks expressed as 2θ at 7.2, 10.9, 13.7, 14.5, 16.7, 19.1, 19.6, 20.8, 21.7, 22.3, 22.8, 23.2, 23.9, 24.5, 24.9, 25.8, 27.0, 27.6, 29.3, 30.3, 30.7, 31.3, 33.4, 38.4 and 39.2 degrees) of efavirenz.

WO patent application publication No. 99/64405 disclosed five crystalline forms, Form 1 (characterized by an x-ray powder diffraction patterns having peaks expressed as 2θ at about 6.0, 6.3, 10.3, 10.8, 14.1, 16.8, 20.0, 20.5, 21.1 and 24.8 degrees), Form 2 (characterized by an x-ray powder diffraction patterns having peaks expressed as 2θ at about 6.8, 9.2, 12.3, 16.2, 21.4, 22.7, 24.1 and 28.0 degrees), Form 3 (characterized by an x-ray powder diffraction patterns having peaks expressed as 2θ at about 7.1, 7.3, 11.0, 13.8, 20.9, 23.3, 27.9 and 33.5 degrees), Form 4 (characterized by an x-ray powder diffraction patterns having peaks expressed as 2θ at about 3.6, 6.3, 9.7, 11.0, 12.7, 13.2, 16.1, 19.2, 19.5, 20.6 and 24.3 degrees) and Form 5 (characterized by an x-ray powder diffraction patterns having peaks expressed as 2θ at about 10.2, 11.4, 11.6, 12.6, 19.1, 20.6, 21.3, 22.8, 24.8, 27.4, 28.2 and 31.6 degrees) of efavirenz.

WO patent application publication No. 2006/018853 disclosed crystalline form H1 and amorphous of efavirenz.

WO patent application publication No. 2006/040643 disclosed the crystalline forms of efavirenz form alpha, form beta, form gamma, form gamma1, form gamma2, form omega, form delta, form N, form O and form P.

WO patent application publication No. WO2008/108630 disclosed the crystalline forms of efavirenz form ULT-1 and form ULT-2.

The known crystalline form H1 disclosed in WO 2006/018853, has been found to be hygroscopic on longer duration of storage. Thus, for example, water content of crystalline form H1 disclosed in WO 2006/018853 is increased by 2.37% in six months studied at the temperature of 25° C. under relative humidity of 60%.

We have found that, when crystalline form H1 is prepared under controlled conditions, the product obtained is non-hygroscopic. The non-hygroscopic nature of form H1 obtained by the process of the present invention is exhibited by the fact that there is no substantial change in the water content even in longer duration of storage and during the pharmaceutical preparations. Thus, for example, water content of crystalline form H1 produced according to the present invention is increased by 0.2% in six months at the temperature of 25° C. under relative humidity of 60%.

According to object of the present invention, therefore, is to provide a process for preparing non-hygroscopic crystalline form H1 of efavirenz, and pharmaceutical preparations comprising non-hygroscopic crystalline form H1 of efavirenz.

DETAILED DESCRIPTION OF THE INVENTION

In accordance with the present invention, a process is provided for preparation of non-hygroscopic efavirenz form H1, which comprises:

a) precipitating from a solution of efavirenz in a $C_1$-$C_6$-alcoholic, $C_3$-$C_8$-ketonic solvent or a mixture thereof by using water as precipitating solvent at below about 15° C., collecting the precipitated solid; and b) air drying the solid collected to obtain non-hygroscopic crystalline efavirenz form H1 wherein the air drying is carried out at about 25° C.-35° C. under relative humidity of 40-80% for 14-25 hours.

The preferable alcoholic solvent is selected from isopropyl alcohol, ethanol, n-propanol, n-butanol and methanol, more preferable alcoholic solvent is isopropyl alcohol.

The preferable ketonic solvent is selected from acetone, methyl ethyl ketone, methyl isobutyl ketone, methyl tert-butyl ketone and diethyl ketone, more preferable ketonic solvent is acetone.

Preferably the precipitation is carried out at about 0° C.-10° C. and more preferably at about 0° C.-5° C.

The precipitated solid may be collected by filtration or centrifugation.

Crystalline form H1 obtained according to the present invention typically has the water content of 2.5-8% by weight of the product obtained, more preferably 3-7% by weight, still more preferably 4-6% by weight as determined by Karl fisher method.

The above crystalline non-hygroscopic form H1 of efavirenz are useful for the preparation of medicaments having nucleoside HIV-1 reverse transcriptase inhibiting activity that is useful in the prevention or treatment of infection by HIV and the treatment of aids. The crystalline non-hygroscopic form H1 of efavirenz can be used in pharmaceutical compositions generally in combination with at least one pharmaceutically acceptable excipient, solid oral dosage forms.

All the patents mentioned above are incorporated herein by reference.

BRIEF DESCRIPTION OF THE DRAWINGS

FIG. 1 is a x-ray powder diffraction spectrum of non-hygroscopic efavirenz form H1.

x-Ray powder diffraction spectrum was measured on a Bruker axs D8 advance x-ray powder diffractometer having a copper-K$\alpha$ radiation.

The following examples are given for the purpose of illustrating the present invention and should not be considered as limitations on the scope or spirit of the invention.

EXAMPLES

Example 1

Efavirenz (10 gm) was dissolved in acetone (40 ml) at 25° C.-30° C., water (410 ml) was added for 45 minutes at 0° C.-5° C. and stirred for 1 hour at the same temperature. Then the separated solid was filtered, washed with water (50 ml) and dried at 25° C.-30° C. under 50-60% relative humidity for 15 hours to obtain 8.2 gm of non-hygroscopic efavirenz form H1.

Example 2

Efavirenz (90 Kg) was dissolved in acetone (360 L) at 25° C.-30° C., added to water (4100 L) for 1 hour 30 minutes at 0° C.-5° C. and stirred for 2 hours 30 minutes at the same temperature. Then the separated solid was filtered, washed with mixture of acetone (10 L) and water (100 L) and dried at 25° C.-30° C. under below 65% relative humidity for 18 hours to obtain 75 Kg of non-hygroscopic efavirenz form H1.

Example 3

Amorphous efavirenz (5 gm) was dissolved in isopropyl alcohol (25 ml) at 25° C.-30° C., water (170 ml) was added for 30 minutes at 5° C.-10° C. and stirred for 1 hour 30 minutes at the same temperature. Then the separated solid was filtered, washed with water (30 ml) and dried at 25° C.-30° C. under 45-55% relative humidity for 20 hours to obtain 4.3 gm of non-hygroscopic efavirenz form H1.

We claim:

1. A process for preparation of the non-hygroscopic efavirenz form H1 which comprises:
    a. precipitating from a solution of efavirenz in a $C_1$-$C_6$-alcoholic, $C_3$-$C_8$-ketonic solvent or a mixture thereof by using water as precipitating solvent at below 15° C., collecting the precipitated solid; and
    b. air drying the solid collected to obtain non-hygroscopic crystalline efavirenz form H1
    wherein the air drying is carried out at 25° C.-35° C. under relative humidity of 40-80% for 14-25 hours.

2. The process as claimed in claim 1, wherein the alcoholic solvent is selected from isopropyl alcohol, ethanol, n-propanol, n-butanol and methanol.

3. The process as claimed in claim 2, wherein the alcoholic solvent is isopropyl alcohol.

4. The process as claimed in claim 1, wherein the ketonic solvent is selected from acetone, methyl ethyl ketone, methyl isobutyl ketone, methyl tert-butyl ketone and diethyl ketone.

5. The process as claimed in claim 4, wherein the ketonic solvent is acetone.

6. The process as claimed in claim 1, wherein the precipitation in step (a) is carried out at 0° C.-10° C.

7. The process as claimed in claim 6, wherein the precipitation is carried out at 0° C.-5° C.

* * * * *